United States Patent [19]

Michel et al.

[11] 4,400,510
[45] Aug. 23, 1983

[54] A-32256 PHENAZINE ANTIBIOTIC

[75] Inventors: Karl H. Michel; Marvin M. Hoehn, both of Indianapolis, Ind.

[73] Assignee: Eli Lilly and Company, Indianapolis, Ind.

[21] Appl. No.: 304,293

[22] Filed: Sep. 21, 1981

Related U.S. Application Data

[62] Division of Ser. No. 144,470, Apr. 28, 1980, Pat. No. 4,316,959.

[51] Int. Cl.$^3$ ..................... C12P 17/12; C07D 241/46
[52] U.S. Cl. .................................................. 544/347
[58] Field of Search ........................................ 544/347

[56] References Cited

U.S. PATENT DOCUMENTS 3,598,819  8/1971  Stapley et al. ..................... 435/121

OTHER PUBLICATIONS

Unezawa, J. Antibiotics 4, pp. 34-40 (1951).
Derwent No. 61595y/35 (Japanese 2083-857) (1978).
Kitahava et al., J. Antibiotics 35, 1412 (1982).
Herzog et al., Chem. Abs. 93, 95296h (1980).

*Primary Examiner*—Mark L. Berch
*Attorney, Agent, or Firm*—Charles W. Ashbrook; Dwight E. Morrison; Arthuyr R. Whale

[57] ABSTRACT

Antibiotic A-32256 which is produced by submerged, aerobic fermentation of a Streptomyces sp. NRRL 12067. The antibiotic has shown antibacterial activity against Staphylococcus and Streptococcus and various anaerobic species. In addition, the antibiotic has shown antitrichomonas activity in vitro, as well as activity for improving ruminant feed efficency and as a mosquito larvacide.

2 Claims, 1 Drawing Figure

A-32256 PHENAZINE ANTIBIOTIC

This application is a division, of application Ser. No. 144,470, filed Apr. 28, 1980 now U.S. Pat. No. 9,316,959.

BACKGROUND OF THE INVENTION

1. Field of the Invention

A large variety of pathogenic microorganisms, such as bacteria and protozoa, are causative agents in producing diseased states in man and animals.

Included in the list of causative agents are such organisms as *Staphylococcus aureus*, *Streptococcus faecalis*, and *Trichomonas vaginalis*.

Although a number of antibiotics have been developed, some of which possess activity against one or more pathogenic organisms, there remains a need for more effective agents to combat the many diseases caused by these organisms in man and animals.

2. Description of the Prior Art

There are a number of antibiotics in the art which contain the phenazine ring system. Among such antibiotics are griseolutein A and griseolutein B, both produced by *Streptomyces griseoluteus*, and reported by Umezawa, *J. Antibiotics* (Japan), 4, 34 (1951). Also in the prior art, antibiotic T-41348, reported in Japanese Pat. No. 2083-857 (Derwent No. 61595Y/35), has a phenazine ring in its structural formula.

Antibiotic A-32256 has a phenazine ring system, but the overall structure of A-32256 differs from those of the prior art antibiotics.

SUMMARY OF THE INVENTION

This invention relates to antibiotic substance A-32256 and to its production by culturing Streptomyces sp. NRRL 12067, or an A-32256-producing mutant or variant thereof, in a culture medium containing assimilable sources of carbon, nitrogen, and inorganic salts, under submerged aerobic fermentation conditions.

The A-32256 antibiotic of this invention inhibits the growth of certain pathogenic microorganisms, in particular those within the genera Staphylococcus and Streptococcus, both genera being gram-positive microorganisms. The A-32256 antibiotic also inhibits the growth of gram-negative anaerobic organisms of the genus Bacteroides, has shown antitrichomonal activity *in vitro*, and inhibits the growht of gram-positive organisms of the genus *Propionibacterium acnes*. Antibiotic A-32256 has shown utility in improving ruminant feed efficiency and as a mosquito larvacide.

DESCRIPTION OF THE DRAWINGS

The infrared absorption spectrum of A-32256 is presented in the accompanying drawing as follows.

DETAILED DESCRIPTION OF THE INVENTION

Figure 1:
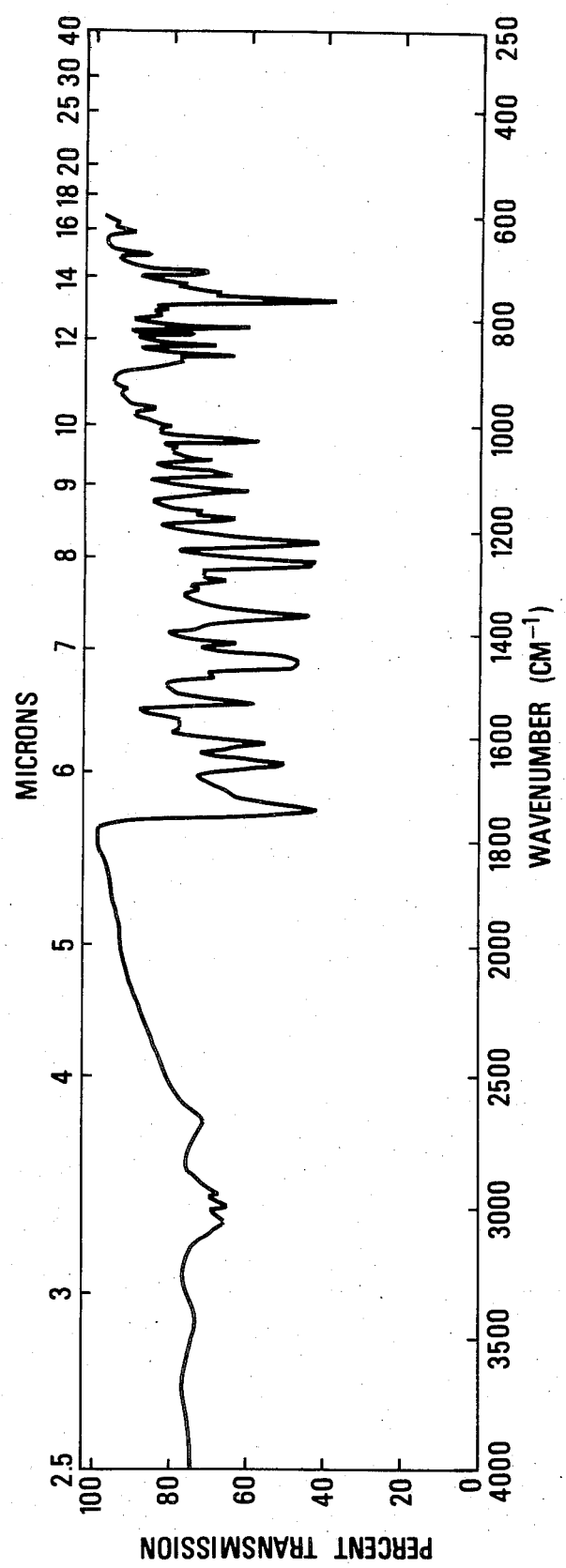
FIG. 1—A-32256 (in KBr pellet)

This invention relates to a novel antibiotic substance and to its preparation. This novel antibiotic has been given the number A-32256 for identification purposes.

This A-32256 antibiotic is produced by culturing a microorganism Streptomyces sp. NRRL 12067, or an A-32256-producing mutant or variant thereof, in a culture medium containing assimilable sources of carbon, nitrogen, and inorganic salts, under submerged aerobic fermentation conditions, until a substantial amount of antibiotic activity is produced. The fermentation mixture is filtered to recover the biomass, i.e., the mycelia, and the filtrate is discarded. The mycelia are stirred with a suitable solvent, such as methanol, to extract the antibiotic from the mycelia. The mycelia are then removed by filtration. The antibiotic is isolated from the filtrate, preferably by extraction with an organic, water-immiscible solvent such as benzene, toluene, or chloroform, followed by concentration of the extract. The antibiotic is separated from the concentrate and purified by column chromatography using silica gel, the column being eluted with a suitable solvent, such as ethyl acetate.

Antibiotic A-32256 is a green, crystalline solid having a melting point of about 196°–198° C. The antibiotic has a molecular weight of 402, as determined by electron-impact mass spectrometry, and an approximate elemental analysis as follows: 68.71% carbon, 4.48% hydrogen, 6.93% nitrogen, and 19.21% oxygen. Based on elemental analysis and molecular weight, an empirical formula of $C_{23}H_{18}N_2O_5$ is assigned to antibiotic A-32256. Potentiometric titration of the novel antibiotic in 66% dimethylformamide in water indicated the presence of two titratable groups with $pK_a$ values of about 5.02 and 7.20 (initial pH 4.1), indicating the antibiotic is capable of forming salts, for example with alkali metals and ammonium. Antibiotic A-32256 has specific rotation of $[\alpha]_D^{25} + 5°$ (c 0.96, chloroform).

A-32256 is easily soluble in chloroform, pyridine, and tetrahydrofuran; moderately soluble in acetone, dioxane, dimethyl sulfoxide and ethyl acetate; sparingly soluble in methanol, ethanol, cyclohexane and hexane; and insoluble in water, but soluble in alkaline aqueous solutions.

The infrared absorption spectrum of antibiotic A-32256 in KBr pellet is shown in the accompanying FIG. 1. The following distinguishable absorption maxima are observed: 3046, 2980, 2934, 2658, 1735, 1646, 1607 (1576, 1565 doublet), 1531, 1481 (shoulder), (1464, 1453 doublet), 1418, 1383 (shoulder), 1363, 1311, 1294, 1282, (1267, 1261 doublet), 1223, 1174, 1161, 1124, 1091, 1065, 1057 (shoulder), 1041, 1029, 1002, 968, 928, 877 (shoulder), 867, 847, 826, 813, 787, 778, 766, 746 (shoulder), 730 (shoulder), 707, 700 (shoulder), 673, 629, 615, 594, and 574 cm$^{-1}$.

The ultraviolet absorption spectrum of antibiotic A-32256 in ethanol under acid, neutral, and basic conditions shows absorption maxima as recorded in Table 1, which follows:

TABLE 1

| UV Spectrophotometry of Antibiotic A-32256 | | |
|---|---|---|
| Acid $\lambda_{max}$ nm($\epsilon$) | Neutral $\lambda_{max}$ nm($\epsilon$) | Basic $\lambda_{max}$ nm($\epsilon$) |
| 400 nm (s)[1] (5,000) | 400 nm (s) (4,800) | 400 nm (s) (10,200) |
| 369 nm (16,100) | 367 nm (15,300) | 364 nm (22,100) |
| 354 nm (s) (11,000) | 354 nm (s) (11,000) | 348 nm (17,400) |
| 320 nm (s) (4,000) | 320 nm (s) (4,200) | 300 nm (15,000) |
| 253 nm (79,200) | 253 nm (80,300) | 254 nm (95,200) |
| 207 nm (52,800) | 207 nm (51,000) | — |

[1](s) = shoulder

X-ray crystallographic study of suitable crystals of A-32256 gave the unit-cell parameters set forth in Table 2, which follows.

TABLE 2

| A-32256 Crystallographic Parameters | |
|---|---|
| $C_{23}H_{18}N_2O_5$ | MW = 402.4 |

TABLE 2-continued

| A-32256 Crystallographic Parameters |
| --- |
| a = 15.812 + 0.005 Å |
| b = 12.845 + 0.003 Å |
| c = 19.619 + 0.006 Å |
| $\beta$ = 99.46 + 0.01° |
| Z = 8 |
| SPACE GROUP: $P2_1/c$ |

The X-ray powder diffraction characteristics of antibiotic A-32256 (copper radiation, 1.5418λ, nickel filter, d=interplanar spacing in angstroms) are recorded in Table 3, which follows:

TABLE 3

X-Ray Diffraction Characteristics for Antibiotic A-32256

| Spacing d(Å) | Relative Intensities $I/I_1$ |
| --- | --- |
| 10.59 | 0.06 |
| 9.36 | 0.50 |
| 8.59 | 0.12 |
| 7.73 | 0.12 |
| 7.34 | 0.21 |
| 6.66 | 0.68 |
| 5.97 | 0.21 |
| 5.68 | 0.12 |
| 5.39 | 0.06 |
| 5.18 | 0.21 |
| 4.97 | 0.15 |
| 4.57 | 0.18 |
| 4.27 | 0.03 |
| 3.89 | 0.21 |
| 3.62 | 1.00 |
| 3.32 | 0.24 |
| 3.22 | 0.06 |
| 3.08 | 0.24 |
| 2.90 | 0.09 |
| 2.73 | 0.06 |
| 2.48 | 0.03 |
| 2.43 | 0.03 |

On the basis of the physical chemical data set forth above, including X-ray crystallography, the structure of antibiotic A-32256 has been determined to be as follows:

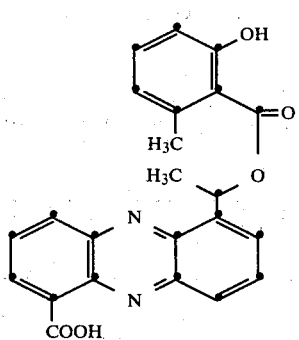

and has been named, following Chemical Abstracts rules of nomenclature, as 6-[1-[(2-hydroxy-6-methylbenzoyl)oxy]-ethyl]-1-phenazinecarboxylic acid.

The Streptomyces sp. culture which is useful for the production of the A-32256 antibiotic was isolated from a soil sample from Yellowstone National Park, and has been deposited and made a part of the stock culture collection of the Northern Regional Research Center, U.S. Department of Agriculture, Agricultural Research Service, Peoria, Ill. 61604, from which it is available to the public under the number NRRL 12067.

As is the case with other organisms, the characteristics of the A-32256-producing culture, Streptomyces sp. NRRL 12067, are subject to variation. For example, natural variants, mutants (spontaneous or induced), transconjugants and recombinants (including recombinant DNA on plasmids) of the NRRL 12067 strain, or derived from this strain, which produce the A-32256 antibiotic may be used in this invention.

A number of different media may be used to produce antibiotic A-32256 with Streptomyces sp. NRRL 12067. For economy in production, optimal yield, and ease of product isolation however, certain culture media are preferred. Thus, for example, preferred carbon sources are glucose, mannitol, maltose, starch, and tapioca dextrin. The optimum level of carbon source is about 2–4%.

Suitable nitrogen source include soybean meal, meat solubles, peanut meal and pork blood meal. A preferred nitrogen substrate is Bacto-peptone (Difco Laboratories, Detroit, Mich.) at a level of 0.7–1.0%.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

The Streptomyces sp. NRRL 12067 culture will produce antibiotic in media that do not contain molasses. However, molasses increases antibiotic yields. Although levels of up to about 4% or more of molasses can be used, an optimum level is about 2%. Molasses can be partially replaced by manganese and several other divalent cations.

Polypropylene glycol having a molecular weight of about 2000–4000, Used at a level of from about 0.1 to about 0.5%, preferably at about 0.25%, increases production of the antibiotic by as much as 100%.

Although small quantities of the A-32256 antibiotic may be obtained by shake-flask culture, submerged aerobic fermentation in tanks is preferred for producing substantial quantities of the A-32256 antibiotic. For tank fermentation, it is preferable to use a vegetative inoculum. The vegetative inoculum is prepared by inoculating a small volume of culture medium with the spore form, mycelial fragments, or a lyophilized pellet of the organism to obtain a fresh, actively growing culture of the organism. The vegetative inoculum is then transferred to a larger tank where, after a suitable incubation time, the A-32256 antibiotic is produced in optimal yield.

The A-32256-producing organism can be grown over a broad temperature range of from about 25° to about 37° C. Optimum production of A-32256 antibiotic appears to occur at a temperature of about 25° C.

As is customary in aerobic submerged culture processes, sterile air is dispersed through the culture medium. For efficient growth of the organism, the volume of the air used in tank production is in the range of from about 0.1 to about 0.5 volumes of air per volume of culture medium per minute (v/v/m), with from about 200 to about 400 RPM agitation. An optimum rate in a 165-liter vessel is about 0.3 v/v/m, with agitation provided by an impeller rotating at about 300 RPM.

Antibiotic activity is generally present after about 48 hours and remains present for at least 10 days during the fermentation period. Peak antibiotic production occurs at from about 7 to about 10 days fermentation time.

Production of the A-32256 antibiotic can be monitored during the fermentation by either agar diffusion or turbidimetric methods. Test organisms suitable for use include *Staphylococcus aureus, Bacillus subtilis,* and *Micrococcus luteus*. The bioassay is preferably performed employing *Staphylococcus aureus* H-Heatley NRRL B-314 in a turbidimetric procedure. Because antibiotic A-32256 is not water soluble, the preferred diluent for use in carrying out the turbidimetric procedure is methanol:water (50:50).

The A-32256 antibiotic can be recovered from the fermentation medium by methods used in the art. At least 95% of the A-32256 antibiotic is normally present in the mycelium. Maximum recovery of the A-32256 antibiotic is accomplished by filtering the whole broth using a filter press and discarding the filtrate. The filter cake is then extracted with a suitable solvent such as methanol. Usually, more than one extraction is done in order to recover the maximum amount of the A-32256 antibiotic. The extracts are combined and concentrated, thus removing a large portion of the methanol, and leaving behind a methanolic aqueous concentrate containing the crude A-32256 antibiotic. This concentrate is extracted with a suitable water-immiscible organic solvent such as benzene, toluene, or chloroform. The extracts are combined and concentrated in vacuo to a small volume.

The crude A-32256 antibiotic is then separated and purified by the use of chromatography such as, for example, high-performance liquid chromatography (HPLC).

Antibiotic A-32256 inhibits the growth of certain microorganisms. The levels at which antibiotic A-32256 inhibits the growth of microorganisms were determined using various testing procedures.

DISC-PLATE SCREENING PROCEDURE

Agar plates, inoculated with the test organism, were used; 6 mm. discs (0.02 ml. capacity) were saturated from log 2 dilutions of the antibiotic solution, or from the solution of the disodium salt of the antibiotic. Disc contents of 1/5 and 1/50 of the concentration of the solution of the antibiotic were used; and disc contents of 1/15 and 1/150 of the concentration of the solution of the disodium salt of the antibiotic were used. Thus, disc contents of 300 and 30 mcg, respectively, were obtained from a solution of 1500 mcg/ml concentration of the antibiotic. Disc contents of 100 and 10 mcg/ml, respectively, were obtained from a solution of 1500 mcg/ml concentration of the disodium salt of the antibiotic A-32256. Activity is reported as the diameter, measured in millimeters (mm.), of the zone of inhibition produced by the different concentrations of antibiotic or its disodium salt in mcg/disc, as recorded in Table 4, which follows.

TABLE 4
ACTIVITY OF ANTIBIOTIC A-32256 AND ITS DISODIUM SALT

| Test Organism | Zone Diameter (mm.) at mcg/disc | | | |
|---|---|---|---|---|
| | A-32256 | | DISODIUM SALT | |
| | 300 | 30 | 100 | 10 |
| *Staphylococcus aureus* 3055* | 26.2 | 23.0 | 25.2 | 17.8 |
| *Staphylococcus aureus* 3074** | 12.2 | 10.0 | 23.3 | 16.2 |
| *Staphylococcus aureus* 3130*** | 30.0 | 25.8 | 26.8 | 19.8 |

TABLE 4-continued
ACTIVITY OF ANTIBIOTIC A-32256 AND ITS DISODIUM SALT

| Test Organism | Zone Diameter (mm.) at mcg/disc | | | |
|---|---|---|---|---|
| | A-32256 | | DISODIUM SALT | |
| | 300 | 30 | 100 | 10 |
| *Streptococcus pyogenes* C203 | 13.0 | 11.0 | 21.0 | 17.0 |
| Streptococcus sp. (Group D) 9960 | 21.0 | 18.2 | 20.4 | 15.6 |
| *Streptococcus pneumoniae* Park I | 16.0 | 14.0 | 31.0 | 25.0 |

*benzylpenicillin-susceptible
**benzylpenicillin-resistant
***methicillin-resistant

AGAR-DILUTION SCREENING PROCEDURE

The agar-dilution procedure described by the International Collaborative Study (ICS) group was used to determine MIC values.

The results obtained from tests of antibiotic A-32256 in the agar-dilution screening procedure are recorded in Table 5, which follows.

TABLE 5
ACTIVITY OF A-32256

| Test Organism | MIC (mcg/ml)[1] |
|---|---|
| *Staphylococcus aureus* 3055* | 1 |
| *Staphylococcus aureus* 3074** | <0.5 |
| *Streptococcus faecalis* X66 | 4 |
| *Erwinia amylovora* | 4 |

*benzylpenicillin-susceptible
**benzylpenicillin-resistant
[1]agar-dilution method Antibiotic A-32256 and its disodium salt are active against anaerobic bacteria, as summarized in Table 6, which follows. The MIC was determined by the agar-dilution method.

TABLE 6
ACTIVITY OF A-32256 AND ITS DISODIUM SALT VS. ANAEROBIC BACTERIA

| Test Organism | MIC (mcg/ml) | |
|---|---|---|
| | A-32256 | Disodium Salt |
| *Actinomyces israellii* W855 | 16 | ≦0.5 |
| *Clostridium perfringens* 81 | 2 | 1.0 |
| *Clostridium septicum* 1128 | ≦0.5 | ≦0.5 |
| *Eubacterium aerofaciens* 1235 | 2 | ≦0.5 |
| *Peptococcus asaccharolyticus* 1302 | 16 | ≦0.5 |
| *Peptococcus prevoti* 1281 | ≦0.5 | ≦0.5 |
| *Peptostreptococcus anaerobius* 1428 | ≦0.5 | ≦0.5 |
| *Peptostreptococcus intermedius* 1264 | ≦0.5 | ≦0.5 |
| *Propionibacterium acnes* 79 | 2 | ≦0.5 |
| *Bacteroides fragilis* 111 | 1 | ≦0.5 |
| *Bacteroides fragilis* 1877 | 8 | ≦0.5 |
| *Bacteroides fragilis* 1936B | 1 | ≦0.5 |
| *Bacteroides thetaiotaomicron* 1438 | ≦0.5 | ≦0.5 |
| *Bacteroides melanogenicus* 1856/28 | 16 | 32 |
| *Bacteroides melanogenicus* 2736 | 16 | ≦0.5 |
| *Bacteroides vulgatis* 1211 | 8 | ≦0.5 |
| *Bacteroides corrodens* 1874 | ≦0.5 | ≦0.5 |
| *Fusobacterium symbiosum* 1470 | 2 | ≦0.5 |
| *Fusobacterium necrophorum* 6054A | 1 | 1.0 |

Antibiotic A-32256 is also active against a genus of anaerobic bacteria identified as *Propionibacterium acnes,* the MIC values being determined by the agar-dilution method, and set forth in Table 7, which follows.

TABLE 7
ACTIVITY OF A-32256 AGAINST PROPIONIBACTERIUM ACNES

| Test Organism | MIC (mcg/ml) |
|---|---|
| P. acnes 44 | ≦0.015 |
| P. acnes 79 | ≦0.015 |
| P. acnes 101 | ≦0.015 |
| P. acnes 103 | ≦0.015 |
| P. acnes 104 | ≦0.015 |
| P. acnes 105 | 0.03 |
| P. acnes 106 | 0.06 |
| P. acnes 107 | ≦0.015 |
| P. acnes 108 | 0.03 |
| P. acnes 5170 | ≦0.015 |
| P. acnes 5176 | ≦0.015 |
| P. acnes 5187 | ≦0.015 |
| P. acnes 5191 | 0.06 |
| P. acnes 5197 | ≦0.015 |
| P. acnes 5226 | ≦0.015 |
| P. acnes 5227 | ≦0.015 |
| P. acnes 5228 | ≦0.015 |
| P. acnes 5229 | 0.03 |
| P. acnes 5246 | ≦0.015 |

*Propionibacterium acnes* and *Staphylococcus aureus*, normally found in the flora of the skin, have been implicated as contributing agents in the more inflammatory types of acne. It is believed *P. acnes* splits the triglycerides in the sebum, thereby liberating free fatty acids and causing the inflammation of acne. In view of the activity shown by antibiotic A-32256 against *S. aureus* and the *P. acnes* in the tests described above, antibiotic A-32256 can be expected to be helpful in alleviating the symptoms of acne through topical application of an effective amount of the antibiotic.

For use in the treatment of acne, the antibiotic can be formulated as a solution, ointment, cream, gel, or salve, or the like, suitable for topical application. These formulations are prepared employing the antibiotic, or a pharmaceutically-acceptable salt thereof, in admixture with any of the conventional formulating ingredients, such as, for example, ethyl alcohol, isopropyl alcohol, acetone, polyvinylpyrrolidone, propylene glycol, fragrance, gel-producing materials, water, benzyl alcohol, stearyl alcohol, stearic acid, sorbitan monooleate, Polysorbate 80, sorbital solutions, methylcellulose, sodium citrate, and sodium lauryl sulfate.

Additional ingredients include from 0 to 50 percent polyethylene glycol (200, 300, 400, 600, etc.); from 0 to 5 percent of a surfactant such as Tween 80; from 0 to 10 percent of a penetrating agent, such as urea or an alkyl methyl sulfoxide; and from 0.5 to 2 percent of a stabilizing agent, such as a buffer, antioxidant, etc. The antibiotic is used in the formulations suitably at concentrations ranging from about 0.001 to about 5 percent by weight.

Antibiotic A-32256 and its disodium salt also showed activity against a genus of anaerobic bacteria identified as *Bacteroides fragilis*, as well as against a few other anaerobic Bacteroides. The MIC values were determined by the agar-dilution method, the endpoints being read 24 hours after incubation, and are recorded in Table 8, which follows.

TABLE 8
ACTIVITY OF A-32256 AND ITS DISODIUM SALT vs. BACTEROIDES SPECIES

| | MIC (mcg/ml) | |
|---|---|---|
| Test Organism | A-32256 | Disodium Salt |
| B. fragilis 1877 | 1.0 | ≦0.015 |
| B. fragilis 103 | 0.5 | ≦0.015 |
| B. fragilis 104 | 1.0 | ≦0.015 |
| B. fragilis 106 | 0.5 | ≦0.015 |
| B. fragilis 107 | 2 | 0.03 |
| B. fragilis 108 | 1.0 | ≦0.015 |
| B. fragilis 110 | 0.5 | ≦0.015 |
| B. fragilis 111 | 1.0 | 0.03 |
| B. fragilis 112 | 0.5 | ≦0.015 |
| B. fragilis 113 | 1.0 | ≦0.015 |
| V. fragilis 1451 | 2 | 0.03 |
| B. fragilis 1470 | 0.5 | ≦0.015 |
| B. fragilis 2 | 1.0 | ≦0.015 |
| B. fragilis 9 | 1.0 | ≦0.015 |
| B. fragilis 62 | 1.0 | ≦0.015 |
| B. corrodens 1874 | 0.25 | ≦0.015 |
| B. vulgatis 1563 | 1.0 | 0.03 |
| B. thetaiotaomicron 1438 | 1.0 | 0.03 |
| B. thetaiotaomicron 1900A | 1.0 | 0.03 |

Antibiotic A-32256 and its disodium salt showed activity against two genera of anaerobic cocci identified as Peptococcus and Peptostreptococcus, respectively. The MIC values were determined by the agar-dilution method, and are recorded in Table 9, which follows.

TABLE 9
ACTIVITY OF A-32256 AND ITS DISODIUM SALT vs. PEPTOCOCCUS AND PEPTOSTREPTOCOCCUS SPECIES

| | MIC (mcg/ml) | |
|---|---|---|
| Test Organism | A-32256 | Disodium Salt |
| Pc.[1] asaccharolyticus 1302 | 2 | ≦0.06 |
| Pc. asaccharolyticus 1344 | 2 | ≦0.06 |
| Pc. constellatus 1468 | 8 | 0.5 |
| Pc. magnus 1401 | 2 | 0.125 |
| Pc. magnus 1421 | 0.5 | 0.125 |
| Pc. magnus 1477 | 0.5 | 0.125 |
| Pc. prevoti 1281 | 2 | 0.125 |
| Pc. prevoti 1293 | 16 | 0.125 |
| Pc. prevoti 1407 | 2 | 0.5 |
| Ps.[2] anaerobius 8 | 2 | 0.25 |
| Ps. anaerobius 52 | 8 | 0.5 |
| Ps. anaerobius 59 | 0.5 | ≦0.06 |
| Ps. anaerobius 1418 | 0.25 | ≦0.06 |
| Ps. anaerobius 1451 | 0.5 | ≦0.06 |
| Ps. anaerobius 1428 | ≦0.125 | 0.25 |
| Ps. anaerobius 1477 | 8 | 0.125 |
| Ps. intermedius 1264 | 2 | ≦0.06 |
| Ps. intermedius 1524 | ≦0.125 | —0.06 |
| Ps. intermedius 1624 | 8 | ≦0.06 |

[1] Pc = Peptococcus
[2] Ps = Peptostreptococcus

Antibiotic A-32256 has shown utility for the improvement of ruminant feed efficiency. Suitable rates of administration are in the range of from about 10 to about 100 g/ton (from about 11 to about 111 ppm) of feed, or from about 0.25 mg to about 2.9 mg/kg of body weight of the ruminant. The preferred level of administration of A-32256 is from about 0.5 to about 1 mg/kg of body weight of ruminant, or about 50 g/ton of feed.

Antibiotic A-32256 is also active as a mosquito larvacide at an application rate of about 20 ppm.

Antibiotic A-32256 disodium salt, when tested by the broth dilution assay against *Trichomonas vaginalis* showed a Minimal Inhibitory Concentration of <0.975 mcg/ml.

In order to illustrate more fully the operation of this invention, the following Examples are provided.

EXAMPLE 1

Preparation of First Stage Inoculum

A medium was prepared for use in the agar slant culture of Streptomyces sp. NRRL 12067:

| Ingredient | Amount (g/L.) |
| --- | --- |
| Tapioca dextrin | 8.0 |
| Enzyme-hydrolyzed casein[1] | 2.0 |
| Beef extract | 1.0 |
| Yeast extract | 1.0 |
| Agar | 20.0 |
| Czapek's mineral stock | 2.0 ml/L. |
| Deionized water | q.s. to 1.0 liter |

[1]N—Z-Amine A (Humko Sheffield Chemical Co., Memphis, Tenn.)

Czapek's mineral stock is prepared from the following ingredients:

| Ingredient | Amount (g/100 ml) |
| --- | --- |
| KCl | 10.0 |
| $MgSO_4.H_2O$ | 10.0 |
| $FeSO_4.7H_2O$ | 0.2 |
| Deionized water | q.s. to 100 ml. |

The pH of the medium was adjusted to 7.3 with 5 N aqueous sodium hydroxide before autoclaving. The pH of the medium after autoclaving was pH 7.0.

Spores of Streptomyces sp. NRRL 12067 were inoculated on a nutrient agar slant made up of the above-identified ingredients, and the thus-inoculated slant was incubated for about 6-7 days at a temperature of about 34° C. The mature slant culture was then covered with sterile distilled water and scraped with a sterile loop to loosen the spores and mycelium. One milliter of the resulting spore suspension was used to inoculate 50 ml. of vegetative medium. An alternate method of providing inoculum for the vegetative medium consisted of substituted a lyophilized pellet for the aqueous spore suspension. Lyophilized pellets were prepared in a manner known in the art. Preparation of the spore suspension for lyophilization was similar to preparation of the aqueous spore suspension, except that sterile calf serum was substituted for sterile distilled water. Composition of the vegetative medium to be inoculated was as follows:

| Ingredient | Amount (g/L.) |
| --- | --- |
| Glucose | 15.0 |
| Tapioca dextrin | 20.0 |
| Soybean meal | 15.0 |
| Corn steep liquor | 10.0 |
| Yeast extract | 1.0 |
| $CaCO_3$ | 2.0 |
| Water | q.s. to 1 liter |

The pH of the medium, 5.6, was adjusted to pH 6.5 with 5 N aqueous sodium hydroxide before autoclaving. The pH of the medium after autoclaving was pH 6.5-6.7.

The vegetative inoculum was incubated in a 250 ml. wide-mouth Erlenmeyer flask at about 30° C. for about 48 hours on a shaker rotating through an arc two inches in diameter at 250 RPM. This incubated medium is used either to inoculate small fermentors (the inoculum being approximately 1% per volume of medium) or to inoculate a second stage medium having the same composition as the vegetative medium for the production of a larger volume of culture.

Fermentation of A-32256

Incubated second-stage medium (800 ml.) thus prepared was used to inoculate 100 liters of sterile production medium having the following composition:

| Ingredient | Amount (g/L.) |
| --- | --- |
| Glucose | 40.0 |
| Molasses | 30.0 |
| Peptone | 10.0 |
| Calcium carbonate | 2.0 |
| Polypropylene glycol* | 2.5 |
| Cold tap water | q.s. to 100 L. |

*Dow-Corning, P2000

The pH of the medium was 6.5 both before and after autoclaving.

The inoculated production medium was allowed to ferment in a 165-liter fermentation tank for about 9 days at a temperature of about 25° C. The fermentation medium was aerated with sterile air at the rate of 0.3 v/v/m and was stirred with conventional agitators at 200-300 RPM.

EXAMPLE 2

Separation of A-32256 Antibiotic

Whole fermentation broth (96 L.), obtained by the procedure described in Example 1, was filtered using 5% filter aid (Hyflo Supercel, a diatomaceous earth, Johns-Manville Products Corporation) in a filter press. The filtrate was discarded. The mycelium was stirred with 30 L. of methanol for about 1 hour at room temperature and again filtered in a filter press, and the filtrate reserved. The mycelium cake was again treated with 30 L. of methanol and the mixture filtered in the filter press, the filtrate being reserved. Each extract was concentrated to a volume of approximately 20 L. Each extract was tested for biological activity using a turbidimetric assay based on activity against a strain of *Staphylococcus aureus*. Both concentrates were found to contain A-32256 antibiotic. The concentrates were combined and further concentrated to a volume of approximately 18 L. This solution was extracted with an equal volume of benzene and the benzene extract was concentrated to a volume of about 1 L. This concentrate contained the antibiotic in crude form.

The benzene solution (1 L.) was concentrated to a volume of about 350 ml and applied to a 7.1-cm × 60-cm column of dry silica gel (Grace 62, mesh size 60-200, Davison Chemical, Baltimore, Maryland). The column was eluted with ethyl acetate at a flow-rate of about 10 ml/min., and 20-ml fractions were collected. An aliquot of each fraction was spotted on silica gel thin layer plates.

The plates were developed in a solvent system of ethyl acetate:methanol (95:5). The antibiotic was detected by short wavelength absorption at 254 nm. Fractions 1-45 were discarded. Fractions 46-80 were combined, filtered, concentrated to a volume of about 25 ml., and kept at about 4° C. for about 16 hours. The crystalline, green precipitate which formed was recovered by filtration and dried under vacuum to yield 850 mg. of product. This preparation was recrystallized from a mixture of chloroform and methanol to yield product having a melting point of about 196°–198° C. This preparation was used for structure determination by X-ray crystallography.

Analyses calculated for $C_{23}H_{18}N_2O_5$:

| Analyses calculated for $C_{23}H_{18}N_2O_5$: | Calculated | Found |
|---|---|---|
| C | 68.65 | 68.71 |
| H | 4.51 | 4.48 |
| N | 6.96 | 6.93 |
| O | 19.88 | 19.21 |

EXAMPLE 3

Preparation of A-32256 Disodium Salt

One gram of A-32256 was dissolved in 50 ml. of a 1:1 (by volume) mixture of methanol and tetrahydrofuran and filtered. This solution was titrated with two equivalents of N aqueous sodium hydroxide. The end point was visible by a color change from green to brown.

This solution was stirred and diluted with 200 ml. of acetone to precipitate the disodium salt of A-32256. The precipitated disodium salt was recovered by filtration. The salt was washed successively on the filter with acetone and diethyl ether and then dried under vacuum. There was obtained 0.996 g. of a brown powder, identified as 6-[1-[(2-hydroxy-6-methylbenzoyl)oxy]ethyl]-1-phenazinecarboxylic acid, disodium salt, monohydrate. The product is hygroscopic.

Analyses calculated for $C_{23}H_{16}N_2O_5 \cdot 2Na \cdot H_2O$:

| Analysis calculated for $C_{23}H_{16}N_2O_5 \cdot Na \cdot H_2O$: | Calculated | Found |
|---|---|---|
| C | 59.59 | 59.67 |
| H | 3.91 | 3.92 |
| N | 6.03 | 5.94 |

We claim:
1. Antibiotic A-32256, a compound of the formula

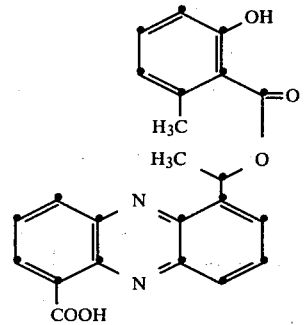

2. The compound identified as 6-[1-[(2-hydroxy-6-methylbenzoyl)oxy]ethyl]-1-phenazinecarboxylic acid, disodium salt, monohydrate.

* * * * *